(12) United States Patent
Oikawa et al.

(10) Patent No.: US 10,638,934 B2
(45) Date of Patent: May 5, 2020

(54) SUBJECT INFORMATION ACCUMULATING APPARATUS

(71) Applicant: CANON KABUSHIKI KAISHA, Tokyo (JP)

(72) Inventors: Katsuya Oikawa, Tokyo (JP); Toshinobu Tokita, Kyoto (JP); Masakazu Toi, Kyoto (JP); Toshiyuki Kitai, Kishiwada (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 636 days.

(21) Appl. No.: 14/368,422

(22) PCT Filed: Dec. 14, 2012

(86) PCT No.: PCT/JP2012/008017
§ 371 (c)(1),
(2) Date: Jun. 24, 2014

(87) PCT Pub. No.: WO2013/099139
PCT Pub. Date: Jul. 4, 2013

(65) Prior Publication Data
US 2014/0350358 A1 Nov. 27, 2014

(30) Foreign Application Priority Data
Dec. 26, 2011 (JP) .................. 2011-283614

(51) Int. Cl.
*A61B 5/00* (2006.01)
*A61B 5/0205* (2006.01)
(Continued)

(52) U.S. Cl.
CPC .......... *A61B 5/0095* (2013.01); *A61B 5/0053* (2013.01); *A61B 5/021* (2013.01);
(Continued)

(58) Field of Classification Search
None
See application file for complete search history.

(56) References Cited

U.S. PATENT DOCUMENTS 5,524,636 A * 6/1996 Sarvazyan ........... A61B 1/0052
600/587
5,678,565 A * 10/1997 Sarvazyan ........... A61B 1/0052
600/437
(Continued)

FOREIGN PATENT DOCUMENTS

CN 101822536 A 9/2010
CN 102137618 A 7/2011
(Continued)

*Primary Examiner* — Joanne M Hoffman
(74) *Attorney, Agent, or Firm* — Canon U.S.A., Inc. IP Division

(57) ABSTRACT

The present invention provides a subject information accumulating apparatus that conducts diagnosis with high reliability.
The subject information accumulating apparatus includes compression plates configured to compress a subject, an irradiation unit configured to apply light, an acoustic wave detector configured to receive acoustic waves generated within a subject and to output an electric signal, and a controller configured to perform control so that an acoustic wave image and pressure information are displayed on a display unit.

13 Claims, 5 Drawing Sheets

(51) Int. Cl.
  *A61B 8/00* (2006.01)
  *A61B 5/021* (2006.01)
  *A61B 5/022* (2006.01)
  *A61B 5/02* (2006.01)
  *A61B 5/1455* (2006.01)

(52) U.S. Cl.
  CPC ......... *A61B 5/0205* (2013.01); *A61B 5/4312* (2013.01); *A61B 5/6843* (2013.01); *A61B 5/708* (2013.01); *A61B 5/743* (2013.01); *A61B 8/4494* (2013.01); *A61B 5/0091* (2013.01); *A61B 5/02* (2013.01); *A61B 5/022* (2013.01); *A61B 5/02233* (2013.01); *A61B 5/14551* (2013.01); *A61B 2562/0204* (2013.01); *A61B 2562/0247* (2013.01); *A61B 2562/046* (2013.01)

(56) References Cited

U.S. PATENT DOCUMENTS

| | | | | |
|---|---|---|---|---|
| 5,833,633 A | * | 11/1998 | Sarvazyan | A61B 1/0052 600/437 |
| 5,860,934 A | * | 1/1999 | Sarvazyan | A61B 1/0052 600/437 |
| 2003/0009101 A1 | * | 1/2003 | Sunagawa | A61B 5/02007 600/437 |
| 2003/0163045 A1 | * | 8/2003 | Gatzke | A61B 5/00 600/437 |
| 2003/0216621 A1 | * | 11/2003 | Alpert | A61B 5/0215 600/300 |
| 2004/0202360 A1 | * | 10/2004 | Besson | G06T 5/008 382/131 |
| 2008/0269606 A1 | * | 10/2008 | Matsumura | A61B 5/0048 600/438 |
| 2010/0036243 A1 | * | 2/2010 | Matsumura | A61B 8/08 600/438 |
| 2010/0198062 A1 | | 8/2010 | Everett et al. | |
| 2011/0071598 A1 | | 3/2011 | McKenna | |
| 2011/0112391 A1 | | 5/2011 | Nishihara | |
| 2012/0078111 A1 | * | 3/2012 | Tanabe | A61B 8/429 600/459 |
| 2013/0028373 A1 | * | 1/2013 | Den Heeten | A61B 6/0414 378/37 |
| 2013/0114371 A1 | * | 5/2013 | Inoue | A61B 8/08 367/11 |

FOREIGN PATENT DOCUMENTS

| | | | | |
|---|---|---|---|---|
| EP | 1554982 A1 | * | 7/2005 | ............ A61B 8/08 |
| JP | 2007-229320 A | | 9/2007 | |
| JP | 2008-191160 A | | 8/2008 | |
| JP | 2009-285345 A | | 12/2009 | |
| JP | 2010-017426 A | | 1/2010 | |
| JP | WO 2010084991 A1 | * | 7/2010 | ........... A61B 5/0091 |
| JP | 2011229756 A | | 11/2011 | |
| WO | 2011/074618 A2 | | 6/2011 | |
| WO | 2011/136153 A1 | | 11/2011 | |

* cited by examiner

[Fig. 1]
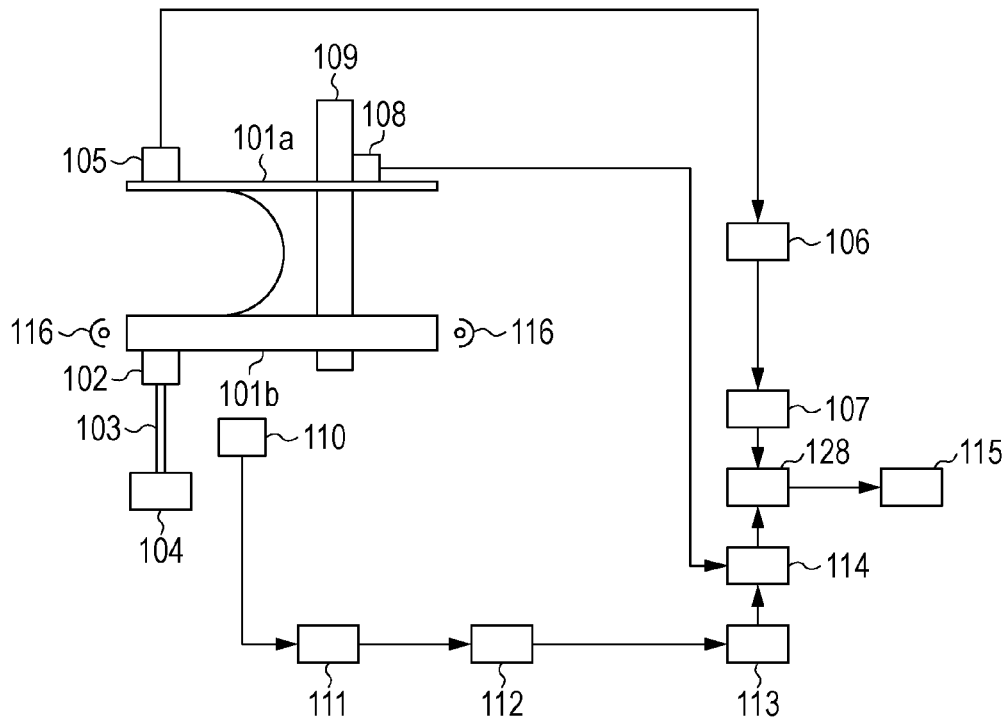
[Fig. 2]
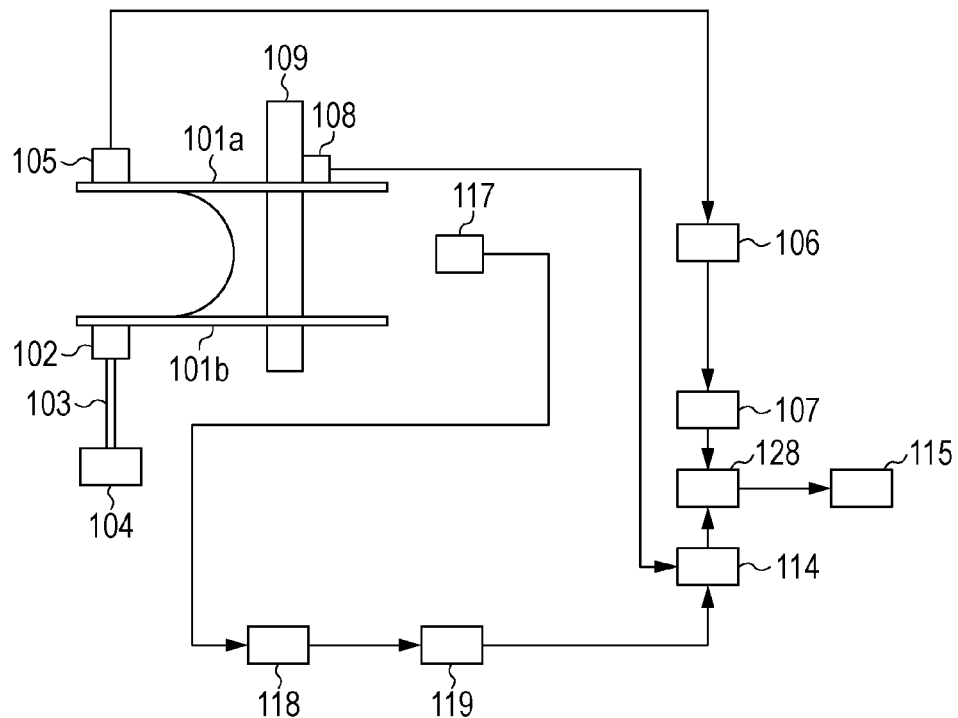

[Fig. 3]
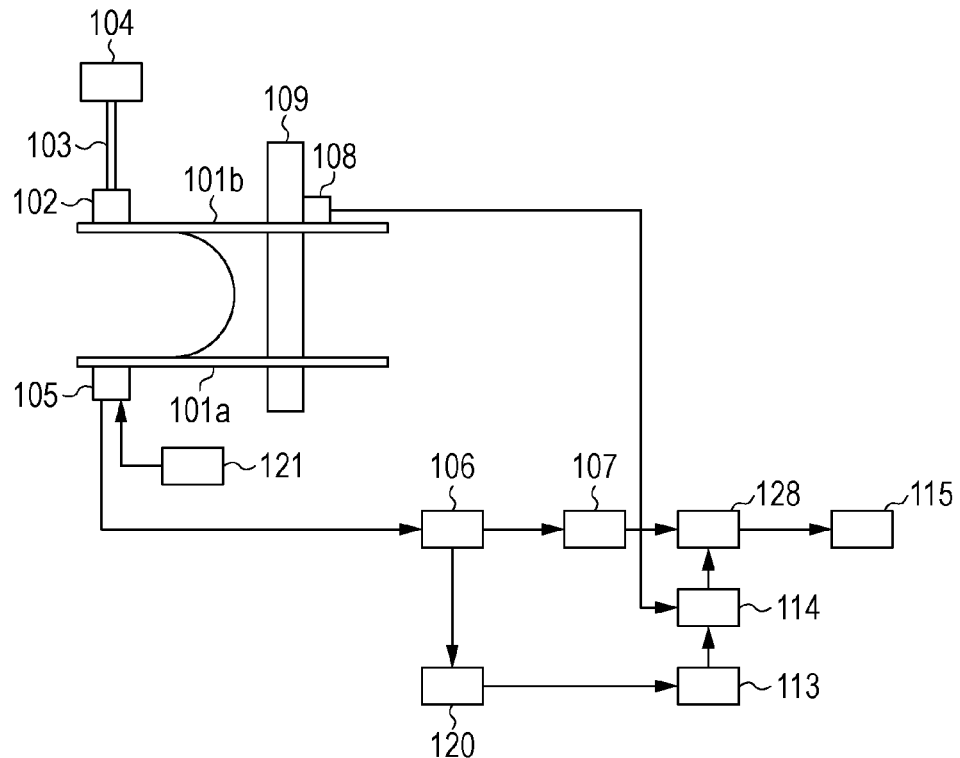
[Fig. 4]
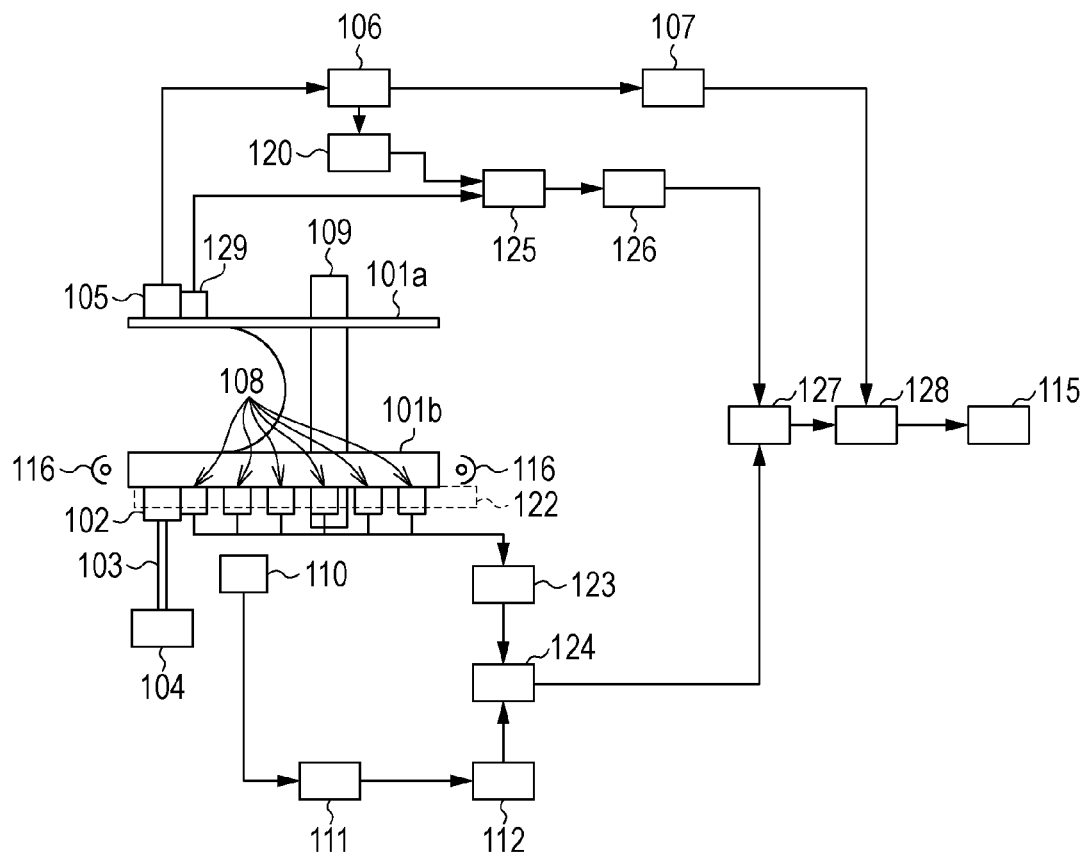

[Fig. 5]
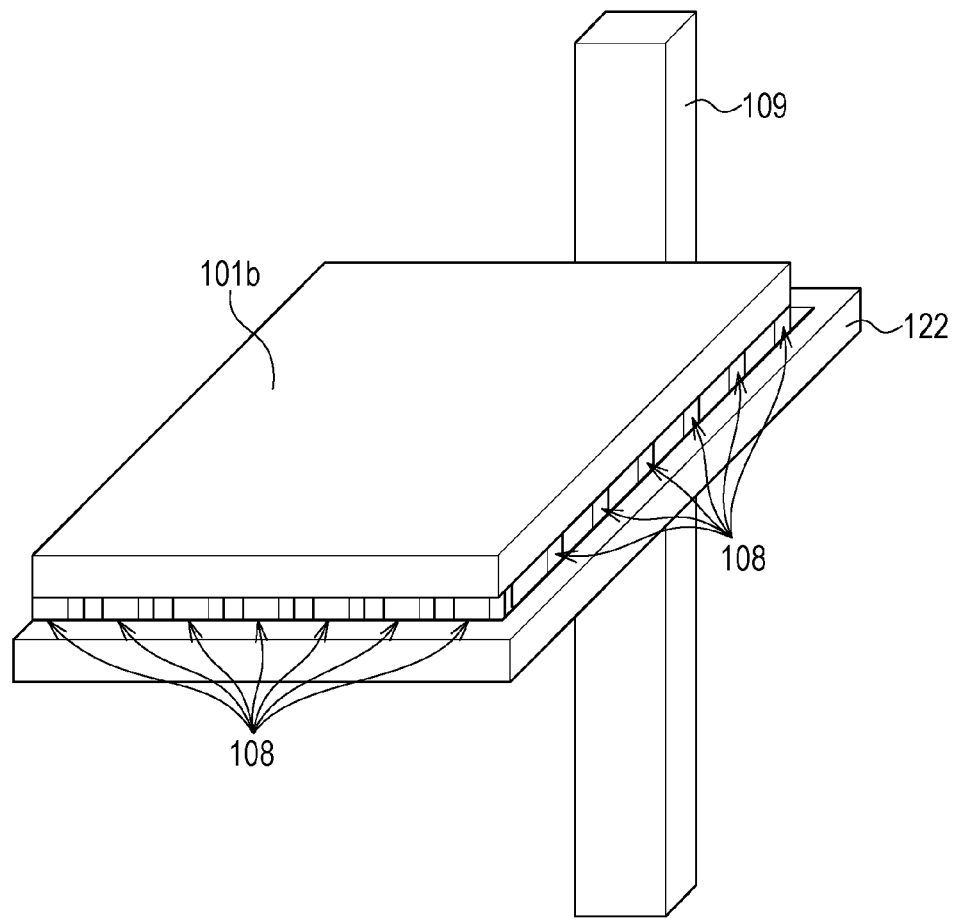
[Fig. 6A]
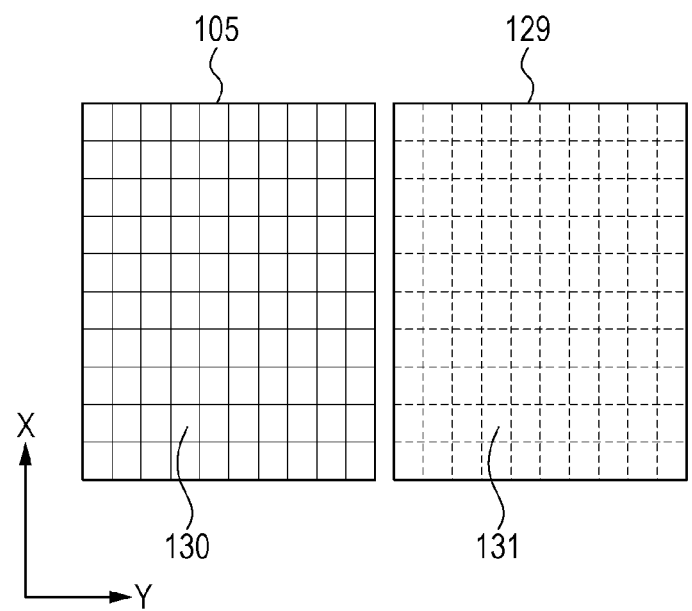

[Fig. 6B]
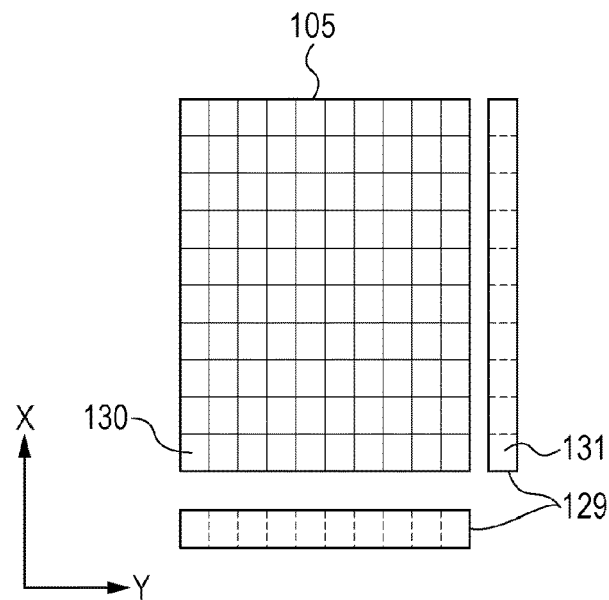
[Fig. 7A]
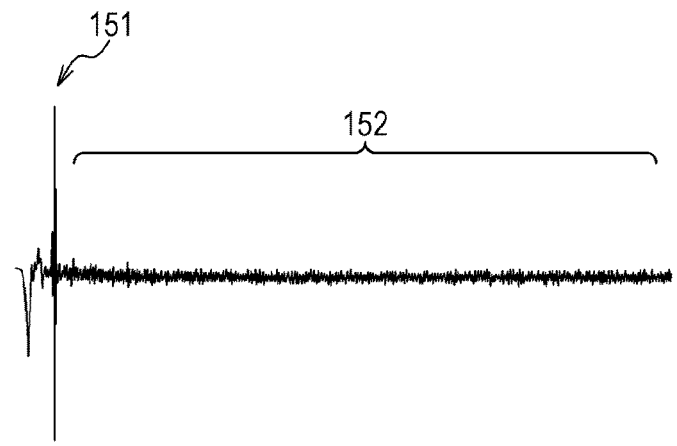
[Fig. 7B]
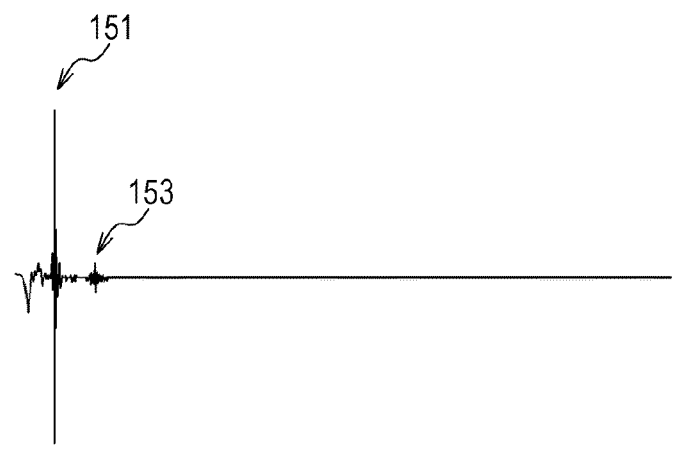

[Fig. 8]
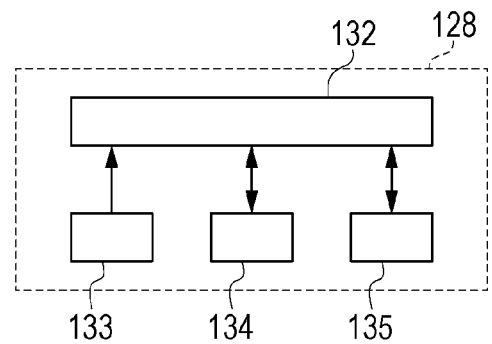
[Fig. 9]
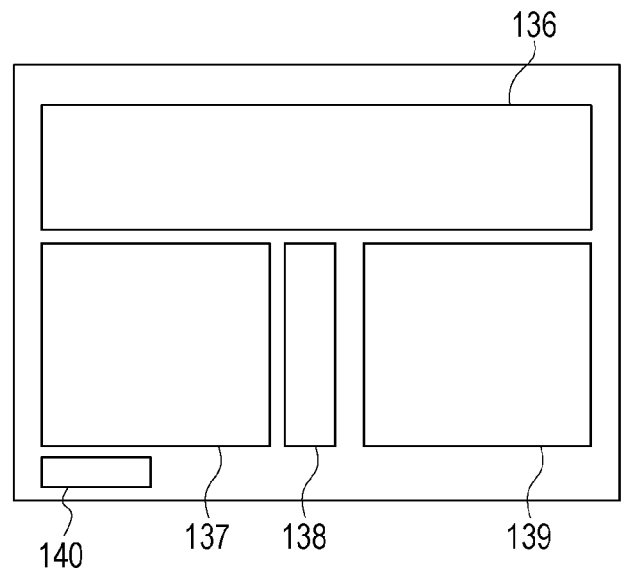

SUBJECT INFORMATION ACCUMULATING APPARATUS

TECHNICAL FIELD

The present invention relates to a photoacoustic wave imaging apparatus that re-constructs three-dimensional images of a subject obtained from photoacoustic waves generated within the subject.

BACKGROUND ART

Hitherto, as a diagnostic imaging apparatus effective for the early detection of breast cancer, an X-ray mammography machine is widely known. In an X-ray mammography machine, a breast is compressed and held between an imaging table storing a radiographic detector therein and a compression plate disposed opposite the imaging table, and the breast is irradiated with X rays through the compression plate. In this case, the reason why the breast is compressed with the compression plate is to reduce the thickness of the breast subjected to an imaging operation so that the required radiation dose for the breast can be minimized. Additionally, in order to ensure the safety for a patient and to prevent an excessive burden from being imposed on the patient caused by the compression of the breast, the load applied to the compression plate is measured and displayed. In this case, however, generally, only the load (force) applied to the compression plate is measured and displayed, and the pressure applied to the breast itself on the compression plate is not considered.

PTL 1 discloses the following X-ray mammography machine. By using a two-dimensional pressure sensor provided in an imaging table, the pressure applied to a breast which is being compressed with a compression plate is measured, and a compression pressure distribution is detected and displayed.

Instead of using X rays involving the radiation exposure, a method for obtaining three-dimensional image data indicating an image of a wide area of a breast by using ultrasonic echoes, which is less invasive than X rays, is known. Additionally, the following photoacoustic mammography machine has recently been suggested. A subject (breast) is irradiated with light in an infrared band, such as laser light having a low biological absorption ratio, and photoacoustic waves generated within the subject are detected. Then, three-dimensional image data formed from the detected photoacoustic waves is obtained and displayed. The photoacoustic mammography machine detects photoacoustic waves which are generated as a result of a specific substance within a subject absorbing energy of light irradiated with the subject and forms an image from the generated photoacoustic waves. Examples of a specific substance within a subject are glucose and hemoglobin contained in the blood. In the photoacoustic mammography machine, the blood distribution within a subject and hemoglobin concentration distribution within the blood may be formed into images. Moreover, as a result of detecting photoacoustic waves generated from a subject irradiated with light having a different wavelength, oxyhemoglobin (oxidized hemoglobin) may be formed into an image. In a known X-ray mammography machine, generally, the X-ray transmittance ratios obtained due to the difference in the tissue density of a subject are formed into an image of a subject internal structure. In contrast, a photoacoustic mammography machine is capable of estimating the density and blood oxygen of a newborn blood vessel generated around a cancer tissue. Thus, the photoacoustic mammography machine is being expected as a modality that conducts cancer diagnosis with higher precision and higher reliability.

PTL 2 discloses the following photoacoustic mammography machine. In order to allow light to reach a deep level of a subject, the subject is irradiated with light in the state in which the subject is compressed between compression plates, and then, photoacoustic waves generated from the subject are obtained.

CITATION LIST

Patent Literature

PTL 1: Japanese Patent Laid-Open No. 2009-285345
PTL 2: Japanese Patent Laid-Open No. 2010-017426

SUMMARY OF INVENTION

Technical Problem

It is desirable to provide a photoacoustic mammography machine that conducts diagnosis with higher reliability than a photoacoustic mammography machine, such as that disclosed in PTL 2.

Solution to Problem

The present invention provides a subject information accumulating apparatus including: compression plates configured to compress a subject; an irradiation unit configured to irradiate a subject with irradiation light; an acoustic wave detector configured to receive acoustic waves generated within a subject irradiated with the irradiation light and to output an electric signal; an image signal generator configured to generate a signal for forming an acoustic wave image on the basis of the electric signal output from the acoustic wave detector;

a pressure information accumulating unit configured to obtain pressure information concerning pressure applied to a subject by the compression plates; and a controller configured to perform control so that the acoustic wave image and the pressure information are displayed on a display unit.

The present invention also provides a subject information accumulating apparatus including: compression plates configured to compress a subject; an irradiation unit configured to irradiate a subject with irradiation light;

an acoustic wave detector configured to receive acoustic waves generated within a subject irradiated with the irradiation light and to output an electric signal; an image signal generator configured to generate a signal for forming an acoustic wave image on the basis of the electric signal output from the acoustic wave detector; a blood pressure information accumulating unit configured to obtain blood pressure information concerning blood pressure of a subject in the state in which the subject is being compressed between the compression plates; and a controller configured to display the acoustic wave image and the blood pressure information on a display unit.

Advantageous Effects of Invention

It is possible to provide a subject information accumulating apparatus that conducts diagnosis with higher reliability.

Further features of the present invention will become apparent from the following description of exemplary embodiments with reference to the attached drawings.

BRIEF DESCRIPTION OF DRAWINGS

FIG. 1 illustrates a configuration of a first embodiment of the present invention.

FIG. 2 illustrates another configuration of the first embodiment of the present invention.

FIG. 3 illustrates a second embodiment of the present invention.

FIG. 4 illustrates a third embodiment of the present invention.

FIG. 5 illustrates an arrangement of load sensors according to the third embodiment of the present invention.

FIG. 6A illustrates an arrangement of a pressure sensor according to the third embodiment of the present invention.

FIG. 6B illustrates another arrangement of pressure sensors according to the third embodiment of the present invention.

FIG. 7A schematically illustrates an ultrasonic echo signal according to the second embodiment of the present invention.

FIG. 7B schematically illustrates an ultrasonic echo signal according to the second embodiment of the present invention.

FIG. 8 illustrates details of a controller according to an embodiment of the present invention.

FIG. 9 illustrates an example of the configuration of display images according to an embodiment of the present invention.

DESCRIPTION OF EMBODIMENTS

Embodiments of the present invention will be described below with reference to the accompanying drawings.

First Embodiment

FIG. 1 illustrates the configuration of a subject information accumulating apparatus according to a first embodiment of the present invention. The subject information accumulating apparatus of the first embodiment includes holding plates 101 (101a, 101b), which serve as compression plates, that hold and compress a subject, a laser light source 104, which serves as an irradiation unit, an ultrasonic transducer array 105, which serves as an acoustic wave detector, a photoacoustic signal processor 106 and a photoacoustic wave image reconstruction unit 107, which serve as an image signal generator, a pressure calculator 114, which serves as a pressure information accumulating unit, and a controller 128. The laser light source 104, which serves as an irradiation unit, applies light to a subject. The ultrasonic transducer array 105, which serves as an acoustic wave detector, receives photoacoustic waves generated within a subject irradiated with light and outputs an electric signal. The photoacoustic signal processor 106 and the photoacoustic wave image reconstruction unit 107, which serve as an image signal generator, generate a signal used for forming a photoacoustic wave image on the basis of an electric signal output from the ultrasonic transducer array 105. The pressure calculator 114, which serves as a pressure information accumulating unit, obtains pressure information concerning pressure applied to a subject with the holding plates 101, which serve as compression plates. The controller 128 performs control so that photoacoustic wave images and pressure information are displayed on a display unit 115. With these elements, the reliability of diagnosis using photoacoustic wave images is improved. This will be described below in a greater detail. A photoacoustic mammography machine, which is a subject information accumulating unit, image information which is useful for examining the blood and the distribution of blood constituents within a subject can be obtained. Accordingly, it can be expected that pressure information concerning the pressure applied to blood vessels and surrounding parts will be used as assisted information during diagnosis. In other words, in the subject information accumulating apparatus, a photoacoustic wave image generated from information concerning the blood of a subject is obtained, and thus, pressure information concerning the pressure applied to the subject is useful for determining the reliability of the obtained photoacoustic wave image. Additionally, the pressure applied to the subject may influence the blood flow, which may impair the reproducibility of measurement of photoacoustic waves. It is thus expected that pressure information will also be used as information for checking the measurement reproducibility.

In a desirable configuration of the subject information accumulating apparatus shown in FIG. 1, the subject information accumulating apparatus also includes an optical transmission unit 103, a light irradiation unit 102, a load sensor (may also be called a "weight sensor") 108, and a support 109. The optical transmission unit 103 includes an optical fiber which transmits light emitted from the laser light source 104. The light irradiation unit 102 irradiates a subject with laser light via the holding plate 101b, which is a compression plate. The load sensor 108 detects a load applied to the holding plate 101a. The support 109 supports the holding plates 101. The subject information accumulating apparatus also includes a charge-coupled device (CCD) camera 110, a CCD camera image generator 111, a contour extracting unit 112, a contact area calculator 113, which serves as a region detector, and an illumination unit 116. The CCD camera 10 is used for accumulating information necessary for the pressure calculator 114 to calculate pressure, and more specifically, to calculate a contact area between each of the holding plates 101 and a subject. In a desirable configuration of the subject information accumulating apparatus shown in FIG. 1, the controller 128 also controls the laser light source 104, the ultrasonic transducer array 105, etc.

The above-described configuration shown in FIG. 1 and the configurations shown in FIGS. 2, 3, and 4, which will be discussed later, are suitable for a subject information accumulating apparatus in order to obtain photoacoustic wave images. This will be described more specifically.

In a subject information accumulating apparatus in which a pressure sensor is disposed on the entire surface of a holding plate, such as the X-ray mammography machine disclosed in PTL 1, it is difficult to accurately irradiate a subject with laser light and to obtain a photoacoustic signal necessary for obtaining photoacoustic wave images, which is a problem unique to a subject information accumulating apparatus for accumulating photoacoustic wave images.

More specifically, a photoacoustic wave is one type of ultrasonic wave, and thus, it is necessary that a subject, a holding plate, and an ultrasonic transducer for detecting photoacoustic waves be disposed in contact with one another acoustically. Particularly, in order to detect weak photoacoustic waves generated within a subject, it is not desirable that materials or structures other than acoustic matched materials be interposed at the interfaces among a subject, a holding plate, and an ultrasonic transducer. The reason for this is as follows. If photoacoustic waves are attenuated and reflected at the contact surfaces among these elements, the intensity of a received photoacoustic signal is decreased, with the result that the signal-to-noise ratio (SNR) is reduced. Additionally, in order to efficiently irradiate a subject with laser light, the optical transparency between a subject and a holding plate has to be high. Accordingly, an irradiation unit that irradiates a subject with laser light is disposed in close proximity with the holding plate, and it is not desirable that materials or structures that cause absorption or reflection of light be disposed between the irradiation unit and the holding plate.

It is also necessary that a pressure sensor constituted by, for example, a piezoelectric element, be disposed in contact with the surface of a subject or a holding plate, in order to directly measure the pressure. However, a solid pressure measurement element, such as a piezoelectric element, generally has a high acoustic impedance, and if it is interposed between a subject and a holding plate, it is likely that intense reflection of photoacoustic waves will occur.

As stated above, in an apparatus for detecting photoacoustic waves as a result of irradiating a subject (breast) fixed with holding plates with light via the holding plates, it is not desirable that a pressure sensor be disposed in a wide area of the surface of a holding plate.

Because of the above-described reasons, the configuration of the subject information accumulating apparatus shown in FIG. 1, which is an example of the first embodiment, and the configurations shown in FIGS. 2 through 4, which will be discussed later, are desirable configurations.

The operation of the subject information accumulating apparatus shown in FIG. 1 will be described below.

A description will first be given of accumulating and displaying of photoacoustic wave images. The two holding plates 101 (101a, 101b), which are supported by the support 109, compress and hold a subject while the interval between the holding plates 101 is being adjusted manually or by being driven by a motor. The holding plate 101b is made from a resin material (e.g., polycarbonate (PC) or polymethyl methacrylate (PMMA)) having a high optical transparency with respect to the wavelength of laser pulse light emitted from the laser light source 104 and an emission wavelength band (visible range) of the illumination unit 116. The holding plate 101a can be made from a material (e.g., polymethylpentene polymer (TPX(R)) having a high transmittance with respect to photoacoustic waves and having an acoustic impedance similar to that of a subject. In this case, a material having an acoustic impedance similar to that of a subject is used in order to prevent photoacoustic waves being reflected at the interface between the holding plate 101a and a subject. The laser light source 104 generates laser light having a specific wavelength of 650 to 1100 nm in response to a driving instruction from the controller 128. The generated laser pulse light propagates through the optical transmission unit 103 and is applied to a subject by the light irradiation unit 102 via the holding plate 101b. Then, photoacoustic waves are generated within the subject irradiated with the laser pulse light and are received by the ultrasonic transducer array 105 via the holding plate 101a. The ultrasonic transducer array 105 opposes the light irradiation unit 102 with the holding plates 101 therebetween, and can be a two-dimensional array. The ultrasonic transducer array 105 and the light irradiation unit 102 may be scanned on the surfaces of the holding plates 101 while keeping opposing each other. The individual elements of the ultrasonic transducer array 105 receive photoacoustic signals. The photoacoustic signal processor 106 then performs signal processing, such as amplification and digitization, on the photoacoustic signals. The acoustic wave image reconstruction unit 107, which forms an image signal generator together with the photoacoustic signal processor 106, converts the photoacoustic signals into three-dimensional image data. On the basis of the photoacoustic signals received from the individual elements of the ultrasonic transducer array 105, the photoacoustic wave image reconstruction unit 107 calculates the intensity levels of photoacoustic waves at individual positions at which they are generated, from the time taken for the photoacoustic waves to reach the elements of the ultrasonic transducer array 105 and from the positions of the elements of the ultrasonic transducer array 105. That is, the photoacoustic wave image reconstruction unit 107 calculates the photoacoustic wave intensity distribution and stores it as three-dimensional image data. The photoacoustic wave intensity distribution may be calculated by using a delay-and-sum method, a back-projection method, or a migration method.

The photoacoustic wave intensity is proportional to the absorption coefficient of pulse light at each point at which a photoacoustic wave is generated. Accordingly, the wavelength of pulse light generated in the laser light source 104 is caused to match the absorption wavelength of the blood, thereby making it possible to create image data representing the blood distribution within a subject. Similarly, the wavelength of pulse light is caused to match the absorption wavelength of hemoglobin, thereby making it possible to create image data representing the hemoglobin concentration distribution. A plurality of pulse light wavelengths may be emitted from the laser light source 104, and photoacoustic waves may be generated in response to the different pulse light wavelengths. Then, upon comparing photoacoustic wave intensity distribution levels obtained in response to the individual pulse light wavelengths with each other, spectroscopic image data may be created. For example, a plurality of pulse light wavelengths are caused to match the absorption wavelengths of oxyhemoglobin and deoxyhemoglobin, and upon comparing photoacoustic wave intensity distribution levels obtained in response to the individual pulse light wavelengths, distribution image data representing the blood oxygen concentration can be created.

The ultrasonic transducer array 105 and the light irradiation unit 102 are scanned on the surfaces of the holding plates 101 by using a scanner (not shown), so that three-dimensional image data representing an image of the entire area of a subject which is in contact with the holding plates 101 can be obtained. The three-dimensional image data created by the photoacoustic wave image reconstruction unit 107 is sent to the controller 128.

The compression pressure applied to a subject is measured as follows.

Desirably, at the time at which a subject is held and fixed by using the holding plates 101, the ultrasonic transducer array 105 and the light irradiation unit 102 move to evacuation positions by using a scanner (not shown). The evacuation positions may be any positions as long as they are outside the angle of view of the CCD camera 110.

The illumination unit 116 including, for example, a light emitting diode (LED) light source, is disposed on the periphery of the holding plate 101b. The holding plate 101b is illuminated by causing illumination light to penetrate into the inside of the holding plate 101b. The CCD camera 110 images the surface of the holding plate 101b. In this case, the major part of the illumination light emitted from the illumination unit 116 propagates through the holding plate 101b while conducting substantially total reflection. The light index is different between a surface of the holding plate 101b which is in contact with a subject (contact surface) and a surface of the holding plate 101b which is not in contact with the subject (non-contact surface). This generates a contrast in an imaging screen of the CCD camera 110. Thus, the contact surfaces of the subject can be detected due to the contrast between the contact surfaces and non-contact surfaces, and particularly, the edges of the boundary between the contact surfaces and the non-contact surfaces are emphasized.

The CCD camera image generator 111 generates captured image information concerning an image obtained by the CCD camera 110, and in this case, the contrast of the brightness of the image may be enhanced. The captured image information is supplied to the contour extracting unit 112, and the contour extracting unit 112 extracts contours of the captured image. Then, the contact area calculator 113, which serves as a region detector, calculates the area within the boundary. More specifically, the contour extracting unit 112 extracts contours by using a spatial-differential filter, and more desirably, it checks for connected portions and non-connected portions of contours and interpolates a boundary between a contact region and a non-contact region with a simply connected boundary line. Then, the contact area calculator 113 counts the number of pixels within the boundary (subject contact region). A method for calculating the contact area of a subject from an image obtained by the CCD camera 110 is not restricted to the above-described method. Various other methods used in normal image processing may be employed, and an image obtained by the CCD camera 110 may be directly binarized without extracting contours.

Image data obtained from the CCD camera image generator 111 may be input into the controller 128, and may be displayed together with a photoacoustic wave image. This will be discussed later.

As the load sensor 108, a load cell device, such as a magnetostrictive load cell, a capacitive load cell, a gyro load cell, or a strain gage load cell, may be used. The load sensor 108, which is provided at a position at which the support 109 supports the holding plates 101, detects the pressure applied to the holding plate 101 and sends a value indicating the detected pressure to the pressure calculator 114, which serves as a pressure information accumulating unit. The pressure calculator 114 calculates the compression pressure from the pressure measured by the load sensor 108 and the subject contact area calculated by the contact area calculator 113. The calculated compression pressure is converted into a unit of mmHg, which can be easily compared with the blood pressure, and is sent to the controller 128.

The controller 128 will be discussed below with reference to FIG. 8. The controller 128 includes a main control unit 132, an input unit 133, an image processor 134, and a storage unit 135.

The main control unit 132 controls an operation for accumulating of photoacoustic waves including the driving of the laser light source 104. Prior to accumulating of photoacoustic wave image data, the main control unit 132 performs control for the above-described compression pressure measurement. Additionally, if photoacoustic wave image data is obtained while scanning the ultrasonic transducer array 105 and the light irradiation unit 102, the main control unit 132 controls an operation for accumulating photoacoustic waves including the driving of a scanner (not shown) and the laser light source 104. Upon receiving various imaging conditions from the input unit 133, the main control unit 132 controls an operation for accumulating photoacoustic wave image data in accordance with the imaging conditions. The main control unit 132 also controls a display image used for creating display image data to be displayed on the display unit 115 in response to an instruction input through the input unit 133. The main control unit 132 is constituted by a central processing unit (CPU) and a microprocessor, such as a micro-processing unit (MPU), for performing the above-described control operations, a random access memory (RAM), a read only memory (ROM), and various buses and communication interfaces for transferring data.

On the basis of three-dimensional image data created by the photoacoustic wave image reconstruction unit 107, the image processor 134 creates a display image, such as a two-dimensional cross-section image, a two-dimensional projection image, or a rendering image, which is specified through the input unit 133, from a photoacoustic wave image. In addition to the type of display image, the position and the direction of the cross section of a two-dimensional cross-section image, the direction of the projection plane of a two-dimensional projection image, the viewing direction of a rendering image, etc. can be specified through the input unit 133. The image processor 134 creates desired display image data in accordance with conditions specified through the input unit 133. The image processor 134 also performs processing, such as noise reduction, filtering, contrast correction, and color correction, on display image data. The image processor 134 may be constituted by a microprocessor similar to that used for the main control unit 132. Desirably, however, a graphic processing unit (GPU), which is specially used for image processing, is used for the image processor 134. In the storage unit 135, various parameters input through the input unit 133 to control the above-described driving operations and display operations, and parameters which are already fixed in the subject information accumulating apparatus are stored. Various items of data are also stored in the storage unit 135. Examples of items of data to be stored in the storage unit 135 are photoacoustic wave image data created by the photoacoustic wave image reconstruction unit 107, pressure value data calculated by the pressure calculator 114, and information concerning a patient, such as an ID and a name of a patient. Further, various items of diagnosis information useful for conducting diagnosis, such as the record of the blood pressure (past maximum and minimum blood pressures, etc.), body fat percentage, body mass index (BMI), age, cup size (difference between the bust size and the band size), are recorded. Images obtained by other modalities, such as X-ray mammography and magnetic resonance imaging (MRI), and past photoacoustic wave images may be transferred through a communication interface of the main control unit 132 and be recorded in the storage unit 135. Moreover, desirably, an image obtained by a different modality that matches a displayed photoacoustic wave image is created by using the image processor 134. For example, if a photoacoustic wave image is displayed as a two-dimensional cross-section image, coordinate transform is performed on a different modality image so that a two-dimensional cross-section image can be formed and displayed together with the photoacoustic wave image in the same cross section. Image data output from the CCD camera image generator 111 and various display images displayed on the display unit 115 may also be stored in the storage unit 135. The storage unit 135 may be constituted by various storage devices, and desirably, a large capacity storage device, such as a hard disk drive (HDD), may be used for storing various items of image data therein.

The main control unit 132 displays display image data indicating a photoacoustic wave image created by the image processor 134 and various items of data stored in the storage unit 135 on the display unit 115. An example of the configuration of various items of display data displayed on the display unit 115 is shown in FIG. 9. In FIG. 9, a patient information display area 136, a photoacoustic wave image display area 137, a photoacoustic-wave-image control parameter display area 138, a different modality image display area 139, and a pressure value display area 140 are shown. In the patient information display area 136, information concerning a patient, such as the patient ID, patient name, past maximum and minimum blood pressures, body fat percentage, BMI, age, and cup size, is displayed. In the photoacoustic wave image display area 137, a photoacoustic wave image, such as a two-dimensional cross-section image, a two-dimensional projection image, or a rendering image, specified through the input unit 133 and created on the basis of three-dimensional image data is displayed. In the photoacoustic-wave-image control parameter display area 138, various conditions for a displayed photoacoustic wave image specified through the input unit 133 are displayed. Examples of the various conditions are the type of display image selected from among a two-dimensional cross-section image, a two-dimensional projection image, and a rendering image, the position and the direction of the section of a two-dimensional cross-section image, the direction of the projection plane of a two-dimensional projection image, and the viewing direction of a rendering image. The content of image processing performed on a displayed photoacoustic wave image, such as the type and various conditions of image filter, and various conditions for correcting the contrast and colors, is displayed. In the different modality image display area 139, an image of a different modality, such as an X-ray mammography or MRI image, and imaging conditions thereof are displayed so that the image of the different modality can be compared with an image displayed in the photoacoustic wave image display area 137. In the pressure value display area 140, the pressure value calculated by the pressure calculator 114 is displayed as the unit of mmHg.

In the different modality image display area 139, instead of displaying a different modality image, for checking the fixing state of a subject between the holding plates 101, an image indicating the appearance of the subject obtained by the CCD camera 110 may be displayed by using image data output from the CCD camera image generator 111. In this configuration of the first embodiment, an image of the appearance of the subject may be displayed next to a photoacoustic wave image, thereby checking the fixing state of the subject when it was imaged.

Display images and various data items displayed on the display unit 115 are stored in the storage unit 135 or are transferred to an external source via a communication interface of the main control unit 132. With this arrangement, when observing a subject over time, photoacoustic wave images can be compared with each other. Additionally, by recording images of the appearances of a subject obtained by the CCD camera 110, the fixing states of the subject when the subject was imaged at different times can be checked.

In the configuration of the subject information accumulating apparatus shown in FIG. 1, the photoacoustic wave image reconstruction unit 107, the CCD camera image generator 111, the contour extracting unit 112, the contact area calculator 113, the pressure calculator 114, and the controller 128 have been described as individual blocks. In reality, however, the processing operations of the above-described blocks can be performed by using software on a personal computer (PC).

As stated above, the measurement of the pressure may be performed prior to accumulating of photoacoustic wave images, or may be performed after the operation for accumulating photoacoustic wave images. Alternatively, the measurement of the pressure may be performed while a photoacoustic wave image is being obtained. In this case, however, the measurement has to be performed at a time at which an image of the entirety of a subject contact surface can be obtained by the CCD camera 110 in accordance with the scanning of the ultrasonic transducer array 105 and the light irradiation unit 102.

In the above-described configuration of the first embodiment, the illumination unit 116 is disposed on the periphery of the holding plate 101$b$, and illumination light propagates through the holding plate 101$b$. However, this configuration is only an example, and another configuration may be employed as long as an image of a subject contact region, particularly, a boundary portion, is clearly obtained by the CCD camera 110 and is detected. For example, the thickness of the holding plate 101$b$ is made thinner, and the holding plate 101$b$ is illuminated from the side on which the CCD camera 110 is disposed, thereby reducing the loss of pulse light penetrated to the inside of a subject from the light irradiation unit 102.

In the above-described configuration, the area of a subject contact region is determined from an image captured by the CCD camera 110. However, the contact area may be calculated by using a different optical imaging device. FIG. 2 is another configuration of a subject information accumulating apparatus including a time-of-flight camera. In FIG. 2, the same elements as those shown in FIG. 1 are designated by like reference numerals (101 through 115). An operation for accumulating and displaying photoacoustic wave images is similar to that discussed above, and an explanation thereof will thus be omitted.

The subject information accumulating apparatus shown in FIG. 2 includes a time-of-flight camera 117, a three-dimensional configuration processor 118, and a contact area calculator 119, which serves as a region detector. The time-of-flight camera 117 measures a three-dimensional configuration of the surface of a subject sandwiched between the holding plates 101. The time-of-flight camera 117 includes a light source, a photo-sensor, and a processor. The light source irradiates a subject with modulated light. The processor performs phase detection on an output from the photo-sensor and measures the distance to a subject from the flight time (delay time) taken for light to be reflected by the subject irradiated with the modulated light emitted from the light source and to reach the photo-sensor and from the velocity of light ($3 \times 10^8$ m/s).

Three-dimensional configuration data indicating a three-dimensional configuration of the surface of a subject obtained by the time-of-flight camera 117 is input into the three-dimensional configuration processor 118. The three-dimensional configuration processor 118 extracts a subject contact region on the basis of position information concerning the positions of the time-of-flight camera 117 and the holding plates 101, which have been measured in advance, and the three-dimensional configuration data indicating a three-dimensional configuration of the surface of the subject. That is, the subject contact region is optically detected by using an optical three-dimensional measuring technique. More specifically, a cross-cap on the surface of a subject and the surface of the holding plate 101 is found as boundary line data indicating a boundary line between a subject contact region and a subject non-contact region, and is input into the contact area calculator 119. The contact area calculator 119 calculates a contact area of the subject positioned on the holding plates 101 on the basis of the boundary line data. The calculated contact area of the subject is used for calculating the pressure, together with the pressure measured by the load sensor 108, as in the configuration shown in FIG. 1.

In the configuration using the time-of-flight camera 117, the contact area of a subject sandwiched between the holding plates 101 is calculated from the three-dimensional configuration of the surface of a subject and the positions of the surfaces of the holding plates 101. Accordingly, the time-of-flight camera 117 can be located at a position at which it can view the space between the holding plates 101. This makes it possible to measure the contact area regardless of the positions of the ultrasonic transducer array 105 and the light irradiation unit 102 located on the holding plates 101. It is thus possible to calculate the pressure applied when a photoacoustic wave image is obtained on time. Additionally, unlike the configuration shown in FIG. 1, in this configuration, the measurement of a contact area is directly performed (not through the holding plate 101), and thus, it is less vulnerable to the influence of errors in measuring a contact area caused by, for example, an unclean surface of the holding plate 101. In the configuration shown in FIG. 2, as well as that shown in FIG. 1, the three-dimensional configuration processor 118 and the contact area calculator 119 are constructed as software in a PC and does not have to be constructed as real circuit blocks.

In the above-described configuration, the contact area is measured by using the time-of-flight camera 117. However, another measuring device that can optically perform a three-dimensional measurement of the surface of a subject, such as a laser-scanning three-dimensional measuring device, may be used. In such a case, advantages similar to those obtained by the use of the time-of-flight camera 117 can be implemented.

In the above-described configuration, a three-dimensional configuration of a subject, which is a breast fixed between the holding plates 101, obtained by using the time-of-flight camera 117 and the three-dimensional configuration processor 118 can be stored in the storage unit 135 within the controller 128 and displayed on the display unit 115. For example, in the example of the display configuration shown in FIG. 9, in accordance with display input settings input through the input unit 133, a three-dimensional configuration obtained when a subject is fixed can be displayed as a rendering image in the different modality image display area 139, together with a photoacoustic wave image, by using data output from the three-dimensional configuration processor 118. If a photoacoustic wave image is displayed as a two-dimensional cross-section image, a two-dimensional projection image, or a rendering image, the position of the section of a two-dimensional cross-section image, the direction of the projection plane of a two-dimensional projection image, the viewing direction of a rendering image can be superposed on the configuration image of the subject displayed in the different modality image display area 139. In the above-described configuration, the position of the appearance configuration of a subject fixed between the holding plates 101 and the position of a displayed photoacoustic wave image are associated with each other, and thus, the positional relationship between a portion to be imaged and the entirety of a subject is clarified. Additionally, as in the configuration shown in FIG. 1, by recording three-dimensional configuration data when a subject is fixed in the storage unit 135 or by transferring it to an external source via a communication interface of the main control unit 132 and storing it in the external source, the fixing states of the subject when the subject was imaged at different times can be compared and checked, as stated above.

In another configuration, the contact area may be measured by using an optical sensor, which performs a scanning operation together with the ultrasonic transducer array 105 and the light irradiation unit 102. In this case, an optical sensor is disposed adjacent to the light irradiation unit 102 such that it faces a subject via the holding plate 101, and detects light reflected by the surface of the subject irradiated with light pulse emitted from the light irradiating unit 102 or light emitted from another light source. Then, a portion at which the amount of reflected light detected by the optical sensor sharply changes is determined as a boundary line between a contact region and a non-contact region of the subject with respect to the holding plate 101, and the contact area of the subject can be calculated from the position of the boundary line, as stated above. The optical sensor may form a plurality of arrays in accordance with the aperture width of the light irradiation unit 102, and a boundary line may be detected by utilizing the positions of individual optical sensors disposed on the arrays and the scanning position of the light irradiation unit 102. In this modification, the contact area of a subject can be calculated with a simpler configuration than the above-described configuration.

As described above, in the first embodiment, the area of an optically imaged subject is detected, and the pressure applied to the holding plate 101 is calculated from the detected area and the pressure value measured by the load sensor 108 disposed at a position at which the support 109 supports the holding plates 101. Accordingly, the light irradiation unit 102 and the ultrasonic transducer array 105 that receives photoacoustic signals can be located in contact with the holding plates 101. With this arrangement, it is possible to calculate the pressure without interfering with the irradiation of laser light to a subject or accumulating of photoacoustic waves from the subject. Moreover, when scanning the light irradiation unit 102 and the ultrasonic transducer array 105, the angle of view of an imaging device, such as the CCD camera 110 or the time-of-flight camera 117, is located outside the scanning range, and thus, the calculation of pressure does not interfere with accumulating of photoacoustic wave images.

Second Embodiment

A subject information accumulating apparatus of a second embodiment will be described below with reference to FIG. 3. The same elements as those of the first embodiment are designated by like reference numerals (101 through 109, 113 through 115, and 128), and an explanation thereof will be omitted or simplified. Details of accumulating and displaying of photoacoustic wave images are similar to that of the first embodiment, and an explanation thereof will thus be omitted. However, the photoacoustic signal processor 106 performs signal processing, such as amplification and digitization, not only on received photoacoustic signals, but also on received ultrasonic wave signals. The subject information accumulating apparatus shown in FIG. 3 includes a transmission wave detector 120 and an ultrasonic wave transmitter 121.

Prior to accumulating of photoacoustic signals, ultrasonic waves are sent and received by the ultrasonic transducer array 105 at the positions of the individual elements of the ultrasonic transducer array 105, thereby detecting a region of a subject in contact with the holding plate 101a within an area in which the subject opposes the ultrasonic transducer array 105. Although a detailed description of the detection operation will be given later, to put it simply, the contact area between a subject and the holding plate 101a is acoustically detected. More specifically, the contact area is detected depending on whether or not ultrasonic waves are received by the ultrasonic transducer array 105. Then, as discussed in the first embodiment, the light irradiation unit 102 irradiates a subject with pulse light, thereby accumulating a photoacoustic signal. If a photoacoustic wave image is obtained by performing scanning, the ultrasonic transducer array 105 and the light irradiation unit 102 are shifted by using a scanner (not shown), and then, at a position at which the ultrasonic transducer array 105 and the light irradiation unit 102 are located after being shifted, detecting of a contact area and accumulating of a photoacoustic signal are repeatedly performed. Then, a contact area of a subject in contact with the holding plate 101a is detected and a photoacoustic signal is obtained. Concerning the order of the detection of a contact area by sending and receiving ultrasonic waves and accumulating of a photoacoustic signal by the irradiation of pulse light, either operation may be performed first.

In response to a drive signal output from the ultrasonic wave transmitter 121, ultrasonic waves are transmitted from some or all of the elements of the ultrasonic transducer array 105 to a subject. The ultrasonic waves pass through the holding plate 101a and enter the inside of the subject at a portion at which the subject contacts the holding plate 101a. Then, ultrasonic echoes are generated within the subject, or the ultrasonic waves are reflected by the opposing holding plate 101b to generate reflected ultrasonic waves. The ultrasonic echoes generated within the subject or the reflected ultrasonic waves are received by the elements of the ultrasonic transducer array 105 positioned at a portion at which the holding plate 101a is in contact with the subject. On the other hand, ultrasonic waves transmitted from the elements positioned at a portion at which the holding plate 101a is not in contact with the subject do not enter the inside of the subject. Instead, multiple reflection occurs within the holding plate 101a, and the elements receive reflected ultrasonic waves. Accordingly, an area in which the subject in contact with the holding plate 101a within a range of a reception region of the ultrasonic transducer array 105 is detected from signals received by the individual elements of the ultrasonic transducer array 105 after transmitting ultrasonic waves.

FIGS. 7A and 7B are schematic diagrams illustrating signals received by the ultrasonic transducer array 105 in response to ultrasonic waves transmitted from the ultrasonic transducer array 105. FIG. 7A illustrates an ultrasonic wave signal received by the elements of the ultrasonic transducer array 105 positioned at a portion at which the holding plate 101a is in contact with a subject, and FIG. 7B illustrates an ultrasonic wave signal received by the elements of the ultrasonic transducer array 105 positioned at a portion at which the holding plate 101a is not in contact with a subject. FIGS. 7A and 7B show a reflected ultrasonic wave signal 151 generated as a result of transmitted ultrasonic waves being reflected on the interface between the subject and the holding plate 101a on the side opposite the side on which the ultrasonic transducer array 105 is provided. FIG. 7A shows an ultrasonic echo signal 152 generated within the subject, and FIG. 7B shows a multiple reflection signal 153 generated as a result of transmitted ultrasonic waves being reflected on the interface between the holding plate 101a and the ultrasonic transducer array 105.

The reflected ultrasonic wave signal 151 is generated due to the difference in the acoustic impedance between the holding plate 101a and the subject, as shown in FIG. 7A, as a result of transmitted ultrasonic waves being reflected at the interface between the holding plate 101a and the subject. Elements of the ultrasonic transducer array 105 positioned at a portion at which the holding plate 101a is in contact with the subject receive this reflected ultrasonic wave signal 151. Thereafter, the ultrasonic echo signal 152 generated in accordance with the tissue within the subject is received. The reflected ultrasonic wave signal 151 is received after the lapse of the time taken for transmitted ultrasonic waves to propagate through the holding plate 101a, and thus, it appears at fixed time intervals at which the individual elements receive the reflected ultrasonic wave signals 151 after the reception start time. After the reflected ultrasonic wave signal 151, the reception of the ultrasonic echo signal 152 continues over the time at which the ultrasonic echo signal 152 propagates almost over the thickness of the subject.

Concerning elements of the ultrasonic transducer array 105 positioned at a portion in which the subject is not in contact with the holding plate 101a, at the interface at which the subject is not in contact with the holding plate 101a on the side opposite the side on which the ultrasonic transducer array 105 is disposed, air contacts the holding plate 101a. A signal received by such elements is shown in FIG. 7B. Generally, the difference in the acoustic impedance between air and the holding plate 101a is greater than that between the subject and the holding plate 101a. Accordingly, a reflected ultrasonic wave signal 151 having a larger intensity is generated at this interface. The ultrasonic waves reflected at this interface travel through the holding plate 101a in the reverse direction, and thus, a multiple reflection signal 153 is generated due to multiple reflection occurring at the interface between the holding plate 101a and the ultrasonic transducer array 105. The time interval between the multiple reflection signal 153 and the reflected ultrasonic wave signal 151 is determined by the thickness of the holding plate 101a and the sonic velocity of ultrasonic waves reflecting within the holding plate 101a. No signal appears at times other than the time at which the multiple reflection signal 153 appears.

As stated above, the transmission wave detector 120 can determine whether a subject is in contact with the holding plate 101a by using a signal appearing at specific positions of a reception signal. More specifically, the transmission wave detector 120 can determine whether a subject is in contact with the holding plate 101a, on the basis of the signal intensity of the reflected ultrasonic wave signal 151 generated at the interface between a subject and the holding plate 101a on the side opposite the side on which the ultrasonic transducer array 105 and the signal intensity of the multiple reflection signal 153 generated at the interface between the holding plate 101a and the ultrasonic transducer array 105. That is, by utilizing the difference in the reflection intensity generated due to the difference in the acoustic impedance between the subject and air, elements that have received a signal having a certain value of reflection intensity or smaller can be determined as elements positioned at a portion at which the holding plate 101a is in contact with the subject.

Additionally, the presence or the absence of the multiple reflection signal 153 within a certain period of time after receiving the reflected ultrasonic wave signal 151 is checked. Then, elements that have received a signal without the multiple reflection signal 153 can be determined as elements positioned at a portion at which the holding plate 101*a* is in contact with the subject.

Moreover, by calculating the signal amplitude intensity over a specific time interval having a certain period of time or longer, the presence or the absence of the ultrasonic echo signal 152 is determined, and elements that have received a signal having the ultrasonic echo signal 152 can be determined as elements positioned at a portion at which the holding plate 101*a* is in contact with the subject. The presence or the absence of the ultrasonic echo signal 152 may be determined by using the average of the signal amplitude intensity over a certain time. However, the ultrasonic echo signal 152 has a characteristic in which it is continuously received, unlike the reflected ultrasonic wave signal 151 and the multiple reflection signal 153. Accordingly, the presence or the absence of the ultrasonic echo signal 152 may be determined by using a time period for which a certain intensity of signal continues. Alternatively, statistical processing may be performed, for example, when the time variance of the signal amplitude intensity with respect to the average signal amplitude intensity is equal to or smaller than a certain value, it may be determined that the ultrasonic echo signal 152 is being received.

All or some of the above-described determination methods may be combined.

The ultrasonic wave signals received by the individual elements of the ultrasonic transducer array 105 are subjected to signal processing, such as amplification and digitization, in the photoacoustic signal processor 106, and are then input into the transmission wave detector 120. The transmission wave detector 120 determines from the digitized ultrasonic wave signals whether the elements of the ultrasonic transducer array 105 have received ultrasonic echoes generated within a subject or ultrasonic waves reflected by the holding plate 101*b*. Then, the transmission wave detector 120 outputs the ID numbers of elements that have received ultrasonic echoes or ultrasonic waves reflected by the holding plate 101*b*, or position information concerning the positions of such elements on the ultrasonic transducer array 105 to the contact area calculator 113.

The contact area calculator 113 calculates the contact area of a subject within the reception region of the ultrasonic transducer array 105 on the basis of the ID numbers or the position information of the elements that have received ultrasonic echoes or reflected ultrasonic waves. For example, if the elements of the ultrasonic transducer array 105 have a uniform area, the contact area of a subject can be determined by multiplying the element area by the number of elements that have received ultrasonic echoes or reflected ultrasonic waves. If the element areas are different, the contact area of a subject can be calculated by considering the element areas of the corresponding elements on the basis of the ID numbers or the position information of the elements. If the ultrasonic transducer array 105 is scanned, the contact areas of a subject at the positions at which the ultrasonic transducer array 105 is located are added to each other, thereby determining the contact area of the subject over the entire scanning region. In this manner, the contact area is acoustically detected.

The calculated contact area of the subject is used for calculating the pressure by using the pressure calculator 114, together with the pressure measured by the load sensor 108, in a manner similar to the first embodiment shown in FIG. 1. Then, in response to an instruction from the controller 128, a photoacoustic wave image and pressure information are displayed on the display unit 115 at the same time.

In the above description, accumulating of photoacoustic signals and sending and receiving of ultrasonic waves for measuring the contact area of a subject are performed by using the same ultrasonic transducer array 105. However, if photoacoustic wave images are obtained by performing a scanning operation, receiving of photoacoustic signals and sending and receiving of ultrasonic waves may be performed by using different transducer arrays. Additionally, processing for received photoacoustic signals and sending and receiving processing for ultrasonic waves may be performed in different blocks.

A photoacoustic signal is one type of ultrasonic wave, and generally, a transducer or a receiver having a wide bandwidth is necessary. It is desired that a transducer that perform both sending and receiving of ultrasonic waves have high receiving sensitivity and also have resistance to high-pressure applied voltages when sending ultrasonic waves.

In order to avoid crosstalk between accumulating of photoacoustic signals and sending and receiving of ultrasonic waves, accumulating of photoacoustic signals for an amount by which photoacoustic waves propagate and sending and receiving of ultrasonic waves for an amount by which ultrasonic waves propagate may be performed at different times independently of each other. Alternatively, the bandwidth used for sending and receiving ultrasonic waves is set to be different from that for photoacoustic waves so as to prevent the occurrence of crosstalk. With this arrangement, accumulating of photoacoustic signals and send and receiving of ultrasonic waves can be simultaneously performed, thereby reducing the total time necessary for accumulating photoacoustic wave images and detecting the contact area.

If accumulating of photoacoustic signals and sending and receiving of ultrasonic waves are simultaneously performed, receiving of photoacoustic waves and sending and receiving of ultrasonic waves are performed in different blocks. It is thus possible to individually set a signal processing band and transducer characteristics for photoacoustic waves and those for ultrasonic waves.

If photoacoustic wave images are obtained by performing a scanning operation and if receiving of photoacoustic signals and sending and receiving of ultrasonic waves are individually performed by using different transducer arrays, the transducer arrays are set at different positions so that a region in which photoacoustic signals are obtained can be different from a region in which the contact area is detected. Accordingly, photoacoustic signals and ultrasonic waves can be spatially separated, thereby preventing the occurrence of crosstalk. In particular, the scanning of a transducer array for receiving photoacoustic waves and the light irradiation unit 102 and the scanning of a transducer array for receiving ultrasonic waves may be performed at the same time, but independently of each other.

In the above-described configuration, the total time necessary for accumulating photoacoustic wave images and detecting the contact area can be reduced. This means that the total time for holding and compressing a subject can be decreased, thereby suitably reducing the burden imposed on a patient.

In the second embodiment, ultrasonic waves are transmitted from the ultrasonic transducer array 105 or another transducer, and echoes generated within a subject is received by the transducer array, thereby detecting a contact region between the holding plate 101*a* and the subject. As a method for acoustically detecting a contact area, a contact portion between a subject and the holding plate 101*a* may be detected by using a received photoacoustic signal. That is, a contact portion between a subject and a holding plate 101a is acoustically detected depending on the presence or the absence of photoacoustic waves received by the ultrasonic transducer array 105. In this case, the photoacoustic signal processor 106 detects a contact area between the holding plate 101a and a subject on the ultrasonic transducer array 105 from photoacoustic signals received by the individual elements of the ultrasonic transducer array 105, in a manner similar to a method for detecting a contact area by using received ultrasonic wave signals. If the ultrasonic transducer array 105 is scanned, the contact regions of a subject at the positions at which the ultrasonic transducer array 105 is located are added to each other, thereby determining the contact area of the subject over the entire region of the holding plate 101a. In this configuration, the ultrasonic wave transmitter 121 is not required, and the contact area of a subject can be calculated at the same time as accumulating photoacoustic wave images.

As described above, in the second embodiment, the area of a subject contact region is detected from a signal received by the ultrasonic transducer array 105 in accordance with whether the holding plate 101a has transmitted ultrasonic waves or photoacoustic waves. The pressure applied to the holding plate 101 is calculated from the detected contact area and the pressure value measured by the load sensor 108 disposed at a position at which the support 109 supports the holding plates 101. With this arrangement, the area of a subject contact region is detected at the same time as the scanning operation for accumulating photoacoustic wave images, and thus, the detection of the area of a subject contact region does not interfere with accumulating of photoacoustic wave images.

Third Embodiment

In a third embodiment, the pressure distribution of each of the holding plates 101a and 101b in a subject contact region is detected. Then, by using the detected pressure distribution, the pressure distribution within the subject is estimated and is displayed together with a photoacoustic wave image at the same time. In this case, the pressure distribution of a subject contact region is detected without interfering with accumulating of photoacoustic signals.

A subject information accumulating apparatus of the third embodiment will be described below with reference to FIG. 4. The same elements as those of the first or second embodiment shown in FIG. 1 or 3 are designated by like reference numerals. A process from receiving a photoacoustic signal to creating three-dimensional image data by using the photoacoustic wave image reconstruction unit 107 performed for accumulating photoacoustic wave image data is similar to that of the first embodiment, and part of an explanation thereof will thus be omitted. The subject information accumulating apparatus shown in FIG. 4 includes a holding frame 122, a weight distribution calculator 123, a light-transmitting-side pressure distribution calculator 124, an ultrasonic-transducer-array pressure measuring unit 125, a photoacoustic-wave-receiving-side pressure distribution calculator 126, a subject pressure distribution calculator 127, which serves as a pressure information accumulating unit, a controller 128, and an array load sensor 129 on which load sensor elements are arranged.

Photoacoustic wave image data is obtained in a manner similar to the first embodiment. The ultrasonic transducer array 105 and the light irradiation unit 102 are positioned such that they oppose each other, and are scanned on the holding plates 101 by a scanner (not shown), thereby accumulating an image of the entire region of a subject.

A description will first be given of the measurement of the pressure distribution of pressure applied to the holding plate 101a which is in contact with a subject within a subject contact region. In the third embodiment, the measurement of the pressure distribution of pressure applied to the holding plate 101a within a subject contact region is performed at the same time as accumulating of photoacoustic wave image data.

The array load sensor 129 is disposed adjacent to the ultrasonic transducer array 105. The size of the array load sensor 129 is large enough to measure the load distribution in a range covering the aperture of the ultrasonic transducer array 105, and the array load sensor 129 desirably detects a load value at a point corresponding to the array position of each of the elements of the ultrasonic transducer array 105. The relative position of the ultrasonic transducer array 105 and the array load sensor 129 is set in accordance with the scanning direction of the ultrasonic transducer array 105.

FIGS. 6A and 6B illustrate specific examples of the element configuration of the ultrasonic transducer array 105, the element configuration of the array load sensor 129, and the positional relationship therebetween.

FIG. 6A illustrates an example of the element configuration of the ultrasonic transducer array 105 and that of the array load sensor 129 when the ultrasonic transducer array 105 is scanned in the y direction in FIG. 6A. As in the ultrasonic transducer array 105 configured as a two-dimensional arrangement, the array load sensor 129 is also configured as a two-dimensional arrangement. Load sensor elements 131 of the array load sensor 129 are disposed at the same pitch interval as those of transducer elements 130 disposed on the ultrasonic transducer array 105. Moreover, the numbers of transducer elements 130 of the ultrasonic transducer array 105 in the vertical and horizontal directions (x and y directions, respectively, in FIG. 6A) are the same as the numbers of load sensor elements 131 of the array load sensor 129, and the ultrasonic transducer array 105 and the array load sensor 129 are disposed side by side in the y direction. When accumulating photoacoustic wave image data, the ultrasonic transducer array 105 is scanned by an amount equal to its width (y direction). With this scanning operation, the positions of the transducer elements 130 disposed on the ultrasonic transducer array 105 are superposed on those of the load sensor elements 131 disposed on the array load sensor 129. Then, the load at a position at which each of the transducer elements 130 was located before the scanning operation can be detected by the associated load sensor element 131.

This will be described more specifically. In synchronization with irradiation of the light irradiation unit 102, photoacoustic waves are received by the individual transducer elements 130 of the ultrasonic transducer array 105, and then, photoacoustic signals are amplified and digitized in the photoacoustic signal processor 106. The transmission wave detector 120 determines, on the basis of the processed signals, whether or not a subject is in contact with the holding plate 101a at a portion at which each of the transducer elements 130 is positioned. At the same time, the load is measured by each of the load sensor elements 31 of the array load sensor 129. The measured load values are stored in the ultrasonic-transducer-array pressure measuring unit 125 for a period of time necessary for scanning the ultrasonic transducer array 105. The ultrasonic-transducer-array pressure measuring unit 125 stores and holds load values measured by the array load sensor 129 while the ultrasonic transducer array 105 is being scanned at one time by an amount equal to its width (y direction). The ultrasonic-transducer-array pressure measuring unit 125 also calculates the pressure values of the transducer elements 130 positioned at a portion at which a subject is in contact with the holding plate 101a, from the load values stored when the previous scanning operation was performed and from a determination as to whether or not a subject is in contact with the holding plate 101a output from the transmission wave detector 120. The ultrasonic-transducer-array pressure measuring unit 125 then outputs the calculated pressure values to the photoacoustic-wave-receiving-side pressure distribution calculator 126. The pressure value of a transducer element 130 positioned at a portion at which a subject is in contact with the holding plate 101a is found by dividing the load value measured by the associated load sensor element 131 of the array load sensor 129 by the area of the associated transducer element 130. The photoacoustic-wave-receiving-side pressure distribution calculator 126 calculates, as the pressure distribution within a contact region, pressure values of the individual transducer elements 130 positioned at portions at which a subject is in contact with the holding plate 101a, on the basis of scanning positional information concerning the scanning position of the ultrasonic transducer array 105 performed for accumulating photoacoustic wave image data.

The above-described operation is performed in accordance with the scanning direction. More specifically, in accordance with the scanning direction, the load values measured by the array load sensor 129 are temporarily stored every time the scanning operation of the ultrasonic transducer array 105 is performed, and the pressure value of each transducer element 130 is calculated by using a determination made by the transmission wave detector 120. However, if the scanning direction is opposite to that described above, a determination as to whether or not a subject is in contact with the holding plate 101a made by the transmission wave detector 120 may be temporarily stored every time the scanning operation is performed. Then, the pressure value of each transducer element 130 may be calculated by using this determination result and the load values measured by the array load sensor 129. If the ultrasonic transducer array 105 is scanned in the x direction, the ultrasonic transducer array 105 and the array load sensor 129 may be arranged side by side in the x direction.

If the ultrasonic transducer array 105 is scanned at one time by an amount equal to the width of one transducer element 130, linear array load sensors 129 may be used, as shown in FIG. 6B. In FIG. 6B, a linear array load sensor 129 is disposed in accordance with the width of one transducer element 130 in each of the x and y directions. Every time the ultrasonic transducer array 105 is moved in each of the x and y directions as a result of a scanning operation, the pressure of one column or one row of transducer elements 130 is measured. This configuration is particularly effective for the following case. If the intensity of a photoacoustic signal used for accumulating photoacoustic wave image data is very weak, the ultrasonic transducer array 105 is scanned at one time by an amount equal to the width of each transducer element 130, and photoacoustic signals output from the transducer elements 130 in overlapping regions are added to each other, thereby contributing to an improvement in the SNR. With this configuration, the pressure distribution in a subject contact region can be detected at the same time as accumulating of photoacoustic wave image data. Moreover, by selecting the numbers of rows and columns of load sensor elements 131 arranged for the array load sensor 129, the measurement of the pressure distribution suitable for a scanning method of the ultrasonic transducer array 105 can be implemented.

In the above-described arrangements, for the sake of a simple description, the pitch interval of the transducer elements 130 disposed on the ultrasonic transducer array 105 is set to be the same as that of the load sensor elements 131 disposed on the array load sensor 129. However, even if the pitch interval is different between the transducer elements 130 and the load sensor elements 131, load values measured by the array load sensor 129 may be interpolated in accordance with a geometric relationship therebetween, thereby making it possible to obtain pressure values at the positions of the transducer elements 130 disposed on the ultrasonic transducer array 105. If an interpolation technique is employed, the transducer elements 130 or the load sensor elements 131 do not have to be spaced uniformly as long as load values can be converted into the pressure distribution by using an interpolation technique in accordance with the size or the arrangement of the transducer elements 130 or the load sensor elements 131. Then, by using the measured pressure values and a determination as to whether a subject is in contact with the holding plate 101a output from the transmission wave detector 120, the pressure distribution can be detected similarly to when an interpolation technique is not employed.

As described above, the array load sensor 129 is disposed adjacent to the ultrasonic transducer array 105, and the pressure distribution is detected in synchronization with a scanning operation of the ultrasonic transducer array 105 for accumulating photoacoustic wave images. Thus, the pressure measurement does not interfere with accumulating of photoacoustic wave images.

A description will now be given of the measurement of the pressure distribution of the holding plate 101b within a subject contact region.

The holding frame 122 holds the periphery of the holding plate 101b via a plurality of load sensors 108, and is movably supported by the support 109. The load sensors 108 are disposed around the holding plate 101b such that they are not in the way of the scanning region of the light irradiating unit 102 and the imaging region of the CCD camera 110. The holding frame 122 moves on the support 109 manually or by being driven by a motor and holds a subject by adjusting the interval between the holding plates 101a and 101b. An example of the arrangement of the load sensors 108, the holding frame 122, and the support 109 which supports the holding plate 101b is shown in FIG. 5. The holding frame 122 may be formed in an angular U shape with one side open to receive a subject, which is a breast, so that it can hold the subject while securing the imaging region. Additionally, the load sensors 108, for example, N load sensors 108, may be disposed along the holding frame 122 at regular intervals, and detect the load distribution levels on the holding plate 101b.

An image of a subject obtained by the CCD camera 110 is processed in the CCD camera image generator 111 and the contour extracting unit 112, in a manner similar to the first embodiment, thereby detecting a region at which the subject is in contact with the holding plate 101b (subject contact region).

The weight distribution calculator 123 calculates the load distribution as follows, on the holding plate 101b on the basis of outputs from the plurality of load sensors 108 disposed along the holding frame 122.

The subject contact region on the holding plate 101b is detected from an output from the contour extracting unit 112. M sampling points are set within the subject contact region. The number M of sampling points may desirably be N−1 (N is the number of load sensors 108 disposed on the holding plate 122) or smaller. The loads at the M sampling points are calculated from the positional relationships between the M sampling points and the N load sensors 108 and outputs from the N load sensors 108.

For example, if the stiffness of the holding plate 101b is high, N equations of moments using each of the load sensors 108 as a pivot point, which is the same number as the number (N) of load sensors 108 are obtained. Moreover, balancing equations of the loads of the M sampling points and the loads of the N load sensors 108 are obtained, and load values at the M sampling points are found as unknown quantities with respect to (N+1) conditional expressions. When M=N+1, the contact load value of a subject at each of the M sampling points is obtained by solving an equation, and when M is not (N+1), the contact load value may be found by using a fitting technique involving a repression analysis, such as the least square method, or by using a statistical method, such as the maximum likelihood estimation.

When M=N+1, the following system of linear equations may be solved by setting load values $P_i$ (i=1, 2, . . . , M) at the M sampling points as unknown quantities.

$$\begin{pmatrix} 1 & 1 & \cdots & 1 & 1 \\ R_{1,1} & R_{1,2} & \cdots & R_{1,M-1} & R_{1,M} \\ R_{2,1} & R_{2,2} & \cdots & R_{2,M-1} & R_{2,M} \\ \vdots & \vdots & \ddots & \vdots & \vdots \\ R_{N-1,1} & R_{N-1,2} & \cdots & R_{N-1,M-1} & R_{N-1,M} \\ R_{N,1} & R_{N,2} & \cdots & R_{N,M-1} & R_{N,M} \end{pmatrix} \begin{pmatrix} P_1 \\ P_2 \\ \vdots \\ P_{M-1} \\ P_M \end{pmatrix} = $$

[Math. 1]

$$\begin{pmatrix} \sum_{j=1}^{N} Q_j \\ \sum_{\substack{j=1 \\ j \neq 1}}^{N} R'_{1,j} Q_j \\ \sum_{\substack{j=1 \\ j \neq 2}}^{N} R'_{2,j} Q_j \\ \vdots \\ \sum_{\substack{j=1 \\ j \neq N-1}}^{N} R'_{N-1,j} Q_j \\ \sum_{\substack{j=1 \\ j \neq N}}^{N} R'_{N,j} Q_j \end{pmatrix}$$

where $R^{i,j}$ is the distance from the i-th (i=1, . . . , M) sampling point to the j-th (j=1, . . . , N) load sensor 108, $R'_{j,k}$ is the distance from the j-th (j=1, . . . , N) load sensor 108 to the k-th (k=1, . . . , N) load sensor 108, and $Q_j$ is the load value measured by the j-th (j=1, . . . , N) load sensor 108.

$$\sum_{\substack{j=1 \\ j \neq k}}^{N}$$

[Math. 2]

represents that the sum of j=1 through j=N is found, except j=k. The right side of the equations denotes vectors in (N+1=M) rows, and the left side of the equations denotes the product of a square matrix arranged in (N+1) rows and M columns, i.e., a square matrix arranged in M rows and M columns, and vectors in M rows. Accordingly, unknown quantities can be found by solving the system of linear equations. Concerning the load values $P_i$ at the M sampling points and the load values $Q_j$ measured by the load sensors 108, the directions of the load acting in opposite directions (e.g., vertical directions in FIG. 4) along the normal line with respect to the surface of the holding plate 101b are set to be positive. Additionally, for adjusting the weight of the holding plate 101b, on the basis of a value before holding a subject, an amount by which the value is increased due to the compression of the holding plate 101b may be used as the load values $Q_j$ measured by the load sensors 108.

When M is not N, the matrix on the left side is not a square matrix. Accordingly, it is not possible to solve the equations. However, by modifying the above-described equations to find $Q_j$ using a fitting technique, the most likelihood value $Q_j$ can be found by using the least square method or another statistical method. In this case, M may be equal to or smaller than N.

If the number M of sampling points is greater than the number N of load sensors 108, the measurement precision is decreased. Thus, on the basis of the load values at the M sampling points obtained as described above, load distribution values at the individual points of the subject contact region on the holding plate 101b may be calculated by using an interpolation method, such as linear interpolation, polynomial interpolation, or wavelet interpolation.

On the basis of the above-described load distribution values, the light-transmitting-side pressure distribution calculator 124 calculates the pressure distribution of a subject contact region on the holding plate 101b. In the third embodiment, the load distribution values at the pixel positions of image data created by the CCD camera image generator 111 are calculated by an interpolation method, and each of the calculated load distribution values is divided by the area of a surface element of the holding plate 101b corresponding to the associated pixel, thereby calculating the pressure value at the associated point of the holding plate 101b in the vertical direction. This operation is performed on the pixels within the subject contact region, thereby calculating the pressure distribution within the entire subject contact region on the holding plate 101b. If necessary, by using every group of multiple pixels as a unit, the load value at the center of the unit is calculated by an interpolation method, and then, the average pressure value is found by dividing the load value at the center of the unit by the area of the multiple pixels, thereby calculating the pressure distribution.

If the stiffness of the holding plate 101b is not sufficiently high so that distortion occurs in the holding plate 101b, the above-described stiff-body moment relationship is not established. However, if the level of distortion of the holding plate 101b is not high, the load distribution can be calculated as follows.

Sampling points are set on the entire surface of the holding plate 101b. Then, a load is applied to a specific sampling point among the set sampling points, and the value of the load is measured by each load sensor 108. In this case, the load applied to a sampling point and the load value measured by a load sensor 108 approximately become linear when the level of distortion is small. That is, the value of a load applied to a specific sampling point and the value measured by a specific load sensor 108 have a linear relationship. Moreover, the influence of the value of a load applied to a different sampling point on the value measured by a specific load sensor 108 is also linear. Based on this fact, the load distribution is calculated as follows.

Values measured by the load sensors 108 when a unit load is independently applied to each of the sampling points disposed over the entre holding plate 101b are stored as a table. This table may be created by actual measurement or may be calculated by using a finite element method using the elasticity value of the holding plate 101b. The value of each of the elements stored in the table serves as a proportionality constant of a linear relationship in which a load applied to a specific sampling point influences a value measured by a certain load sensor 108.

By using, among the sampling points stored in the table, sampling points contained in a subject contact region on the holding plate 101b, equations which find values measured by the individual load sensors 108 can be established as follows on the basis of the above-described linear relationship. In the equations, the number of sampling points contained in the subject contact region are denoted by M', and the number of load sensors 108 are denoted by N.

$$\begin{pmatrix} C_{1,1} & C_{1,2} & \cdots & C_{1,M'-1} & C_{1,M'} \\ C_{2,1} & C_{2,2} & \cdots & C_{2,M'-1} & C_{2,M'-1} \\ \vdots & \vdots & \ddots & \vdots & \vdots \\ C_{N-1,1} & C_{N-1,2} & \cdots & C_{N-1,M'-1} & C_{N-1,M'} \\ C_{N,1} & C_{N,2} & \cdots & C_{N,M'-1} & C_{N,M'} \end{pmatrix} \begin{pmatrix} P_1 \\ P_2 \\ \vdots \\ P_{M'-1} \\ P_{M'} \end{pmatrix} = \begin{pmatrix} Q_1 \\ Q_2 \\ \vdots \\ Q_{N-1} \\ Q_N \end{pmatrix}$$

[Math. 3]

where $P_i$ (i=1, 2, ..., M') is a load value at a sampling point contained in a subject contact region, $Q_j$ is a load value measured by the j-th (j=1, ..., N) load sensor 108, and $C_{i,j}$ is a proportionality constant, which is an element in the above-described table, of a load value applied to the i-th sampling point and a value measured by the j-th load sensor 108.

When M' is equal to or smaller than N, in a manner similar to the case in which the above-described stiff-body moment relationship is established, the load value $P_i$ at a sampling point contained in the subject contact region is calculated from the load value $Q_j$ measured by the load sensor 108 by using a system of linear equations or a fitting technique, and the calculated load values $P_j$ are interpolated in a manner similar to that discussed above, thereby determining the pressure distribution within the subject contact region.

When the number M' of sampling points contained in the subject contact region is greater than the number N of load sensors 108, sampling points used for determining the load distribution are selected so that the number M' of sampling points becomes equal to or smaller than N. Then, the load distribution is calculated. The light-transmitting-side pressure distribution calculator 124 determines the pressure distribution within the subject contact area by interpolating the load values.

A description has been given above, assuming that a value measured by the load sensor 108 is a load, i.e., a normal stress occurring along a normal line with respect to the surface of the holding plate 101b. Alternatively, a value measured by the load sensor 108 may be a stress occurring along a normal line with respect to a cross section of the holding plate 101b, a shear stress occurring with respect to a cross section, or various types of distortions. In those cases, there is also a linear relationship between values measured by the load sensors 108 and loads applied to sampling points. Accordingly, linearity relational expressions using matrices similar to those described above are established, and thus, the load distribution can be found by performing calculations similar to those described above. Particularly, among various types of distortions and stresses, by using a plurality of independent stresses, the number N of values measured by the load sensors 108 can be increased. This makes it possible to increase the number M' of sampling points used for calculating the above-described load distribution. As a result, the precision in calculating the pressure distribution determined by using interpolation can be improved.

With the above-described configuration, the pressure distribution within a subject contact region of the holding plate 101b is calculated by using the load sensors 108 disposed outside the scanning region of the light irradiation unit 102 and the imaging region of the CCD camera 110. That is, the pressure distribution is detected by using the load sensors 108 installed in a region which is not in the way of the scanning operation of the light irradiation unit 102 for accumulating photoacoustic wave images. Thus, the measurement of the pressure distribution which does not interfere with accumulating of photoacoustic wave images is implemented.

The pressure distribution within a subject contact plane on each of the holding plates 101a and 101b calculated as described above is output to the subject pressure distribution calculator 127, which serves as a pressure information accumulating unit. Then, pressure distribution information concerning the pressure distribution of the pressure applied to a subject by each of the holding plates 101a and 101b, which are compression plates, is obtained.

Three-dimensional photoacoustic wave image data created by the photoacoustic wave image reconstruction unit 107 is converted into display photoacoustic wave image data in accordance with a display image format selected by the controller 128, in a manner similar to the first embodiment. Examples of the display image format are a maximum intensity projection (MIP) image in a specified direction, a tomographic image of a specified cross section, and surface rendering or volume rendering concerning a specified threshold. Brightness or color values are input into coordinates of a projection surface, a cross section, or rendering image data in accordance with a display image format specified on the basis of one of the elements, such as the photoacoustic wave generation intensity, laser light absorption intensity, hemoglobin concentration, or blood oxygen concentration calculated by the photoacoustic wave image reconstruction unit 107, or the distribution of each of the elements. Then, brightness or color value data is created.

On the basis of the pressure distribution within a subject contact plane on each of the holding plates 101a and 101b obtained by the photoacoustic-wave-receiving-side pressure distribution calculator 126 and the light-transmitting-side pressure distribution calculator 124, respectively, the subject pressure distribution calculator 127, which serves as a pressure information accumulating unit, calculates pressure distribution image data concerning the pressure distribution at the points within a subject in accordance with a display image format selected by the controller 128. In this case, the display image format may be the same as that used for creating display photoacoustic wave image data, or may be different from that used for creating display photoacoustic wave image data. If the two display image formats are the same, a pressure distribution image and a photoacoustic wave image can be compared easily. For example, if a specific cross section is specified for a display photoacoustic wave image, cross-section pressure distribution data indicating the pressure distribution on the same cross section is calculated by the subject pressure distribution calculator 127. For calculating the pressure distribution data, an interpolation operation, such as linear interpolation, polynomial interpolation, or wavelet interpolation, is performed at the points on the specified cross section, on the basis of the pressure distribution in the subject contact plane on each of the holding plates 101a and 101b.

If a photoacoustic wave image is created as an MIP image in a specified direction, an MIP image indicating pressure distribution in the same direction as the specified direction is calculated by using an interpolation method. Then, the created pressure MIP image can be easily compared with a photoacoustic wave image. If a rendering photoacoustic wave image is displayed, pressure surface rendering data or pressure volume rendering data is created. However, the display image format of a pressure distribution image does not necessarily have to be the same as that of a photoacoustic wave image.

The calculated section pressure distribution data is sent to the controller 128. Then, in a manner similar to a photoacoustic wave image, pressure values at the individual points of the pressure distribution data are converted into brightness or color value data to be displayed. The converted data is displayed with a display photoacoustic wave image on the display unit 115 at the same time. If a photoacoustic wave image and a pressure distribution image are displayed in the same display image format at the same time, particularly by being superposed on each other, pressure information and photoacoustic information located at substantially the same position can be compared. However, a photoacoustic wave image and a pressure distribution image in different image formats may be displayed for comparison, or they may be displayed at the same time separately or at different times. As discussed above, the main control unit 132, the input unit 133, the image processor 134, and the storage unit 135 are provided in the controller 128, as shown in FIG. 8. On the display unit 115, as shown in FIG. 9, various areas are shown, such as the patient information display area 136, the photoacoustic wave image display area 137, the photoacoustic-wave-image control parameter display area 138, the different modality image display area 139, and the pressure value display area 140.

As in the first embodiment, these items of cross-section pressure distribution data are stored in the storage unit 135 of the controller 128, and are processed in the image processor 134 in accordance with a display image format specified by a display control input operation performed on the input unit 133. The cross-section pressure distribution data is then displayed on the display unit 115. In the display configuration shown in FIG. 9, for example, a pressure distribution image may be displayed as pressure contour lines or a color region by being superposed on a display photoacoustic wave image displayed in the photoacoustic wave image display area 137. In the different modality image display area 139, a pressure distribution image may be displayed as a color region, next to a displayed photoacoustic wave image. In this case, it is desirable that the position or the viewpoint direction of a cross section of a pressure distribution image match that of a photoacoustic wave image. This can be performed in a manner similar to a matching operation for matching a different modality display image with a photoacoustic wave image in the first embodiment. In the pressure value display area 140, an average pressure value may be displayed.

As described above, the two-dimensional pressure distribution within a subject contact region on the holding plate 101a is calculated by using the array load sensor 129 which is scanned simultaneously with the ultrasonic transducer array 105, while the two-dimensional pressure distribution within a subject contact region on the holding plate 101b is calculated by using the load sensors 108 disposed on the holding frame 122. Accordingly, in this configuration, the pressure distribution within a subject contact region on the holding plate 101b is optically detected, while the pressure distribution within a subject contact region on the holding plate 101a is acoustically detected. Thus, the configuration of the subject information accumulating apparatus of the third embodiment has a high affinity with a photoacoustic wave image accumulating operation.

However, the two-dimensional pressure distribution within a subject contact region both on the holding plates 101a and 101b may be calculated by using the load sensors 108 disposed on the holding frame 122.

Alternatively, the two-dimensional pressure distribution within a subject contact region on the holding plate 101b may be calculated as follows. Scanning is performed by using a combination of an ultrasonic probe that is capable of sending and receiving ultrasonic waves and an array load sensor, and then, ultrasonic echoes are received, and transmitted waves are detected. The pressure on an ultrasonic transducer array is then measured.

Alternatively, a two-dimensional pressure distribution obtained by scanning an ultrasonic probe that is capable of sending and receiving ultrasonic waves and an array load sensor may be compared with a subject contact region obtained by the CCD camera 110, thereby accumulating a two-dimensional pressure distribution within a subject contact region.

In another configuration, a CCD camera 110 that is capable of detecting polarization may be used, and a photoelastic image of the holding plate 101b may be obtained by the CCD camera 10, thereby accumulating a relative stress distribution on the holding plate 101b. Then, by using the relative stress distribution and a compression force of the holding plate 101b measured by a load sensor, a two-dimensional pressure distribution within a subject contact region on the holding plate 101b may be calculated.

In the third embodiment, a two-dimensional pressure distribution within a subject contact region on the holding plate 101a and that on the holding plate 101b are separately calculated. Accordingly, the pressure within a subject can be measured even if the area of a subject contact region on the holding plate 101a and that on the holding plate 101b when holding and compressing a subject are different from each other. This is particularly effective, for example, when holding plates are horizontally placed in a direction perpendicular to the gravity. More specifically, in this case, the area of a subject contact region may become different between the top and bottom holding plates due to the influence of the weight of a subject or due to the nonuniform compression force. In particular, even when there is a difference in the pressure between the holding plates since the area of a subject contact region on one holding plate is different from that on the other holding plate, the distribution of pressure values at a portion extracted from a photoacoustic signal, for example, in a cross section of a photoacoustic wave image, can be displayed with the photoacoustic wave image at the same time. As a result, it is possible to effectively utilize pressure distribution information concerning the pressure distribution within a subject for conducting diagnostic imaging on blood distribution, hemoglobin concentration distribution, blood oxygen concentration distribution, etc., using photoacoustic wave images.

In all of the first through third embodiments, instead of or in addition to pressure information, blood pressure information may be displayed. More specifically, by using a known blood pressure information accumulating unit (sphygmomanometer), the blood pressure of a patient is measured and is displayed together with a photoacoustic wave image. In this case, the blood pressure of a patient in the state in which a subject of the patient is compressed between holding plates may be measured, and blood pressure information may be displayed together with a photoacoustic wave image on the display unit 115. In such a case, advantages similar to those when pressure information is displayed can be implemented. The state in which a subject of a patient is compressed between holding plates is not restricted to a state while a subject is being compressed between holding plates. If the relationship between the blood pressure information while a subject is being compressed and that before or after the compression of the subject is clarified, the blood pressure information before or after the compression of the subject and a photoacoustic wave image can be displayed on the display unit 115, which serve as sufficiently effective information for determining the reliability of the photoacoustic wave image. In this case, it is desirable that blood information be displayed with a photoacoustic wave image together on the display unit 115 at the same time, in a manner similar to pressure information.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-283614, filed Dec. 26, 2011, which is hereby incorporated by reference herein in its entirety.

The invention claimed is:

1. A subject information obtaining apparatus comprising:
   first and second compression plates configured to compress a subject wherein the first and second compression plates include first and second pressure sensors, respectively;
   an irradiation unit configured to irradiate the subject with irradiation light via the second compression plate;
   an image signal generator configured to generate a signal for forming an acoustic wave image in a subject held by the first compression plate and the second compression plate;
   an acoustic wave detector positioned opposite the irradiation unit, the acoustic wave detector configured to receive acoustic waves via the first compression plate, the acoustic waves being generated within the subject irradiated with the irradiation light, and to output an electric signal, wherein
   the image signal generator configured to generate the signal for forming the acoustic wave image on the basis of the electric signal output from the acoustic wave detector;
   a first pressure calculator configured to obtain first pressure distribution information within a subject contact plane on the first compression plate based on the first pressure sensor;
   a second pressure calculator configured to obtain second pressure distribution information within the subject contact plane on the second compression plate based on the second pressure sensor;
   a pressure information obtaining unit configured to obtain a pressure distribution image using the first pressure distribution information from the first pressure calculator and the second pressure distribution information from the second pressure calculator; and
   a controller configured to cause a display unit to display a tomographic image of the subject and the pressure distribution image.

2. The subject information obtaining apparatus according to claim 1, wherein the pressure information obtaining unit obtains the first and second pressure distribution information as a distribution image data within the subject.

3. The subject information obtaining apparatus according to claim 1, further comprising an input unit that allows an input to specify a cross section to be displayed on the display unit.

4. The subject information obtaining apparatus according to claim 1, further comprising:
   a region detector configured to detect a contact region based on contrast between the contact region and a non-contact region.

5. The subject information obtaining apparatus according to claim 1, wherein the controller is further configured to display at least one from a group of items including body fat percentage, BMI, age, and cup size, ID of the subject.

6. The subject information obtaining apparatus according to claim 1, further comprising:
   a scanning unit that moves the acoustic wave detector and the irradiation unit relative to the subject.

7. The subject information obtaining apparatus according to claim 1, wherein the controller causes the display unit to display the tomographic image and the first and second pressure distribution information in an overlapped manner.

8. The subject information obtaining apparatus according to claim 4, wherein the region detector optically detects the contact region.

9. The subject information obtaining apparatus according to claim 8, wherein the region detector optically detects the contact region by using optical imaging or optical three-dimensional measurement performed through the first and second compression plates.

10. The subject information obtaining apparatus according to claim 4, wherein the region detector acoustically detects the contact region.

11. The subject information obtaining apparatus according to claim 10, wherein the region detector acoustically detects the contact region in accordance with whether an ultrasonic transducer array has received ultrasonic waves or acoustic waves.

12. The subject information obtaining apparatus according to claim 1, further wherein the controller causes the tomographic image and the first and second pressure distribution information of a cross-section to be displayed in an overlapped manner.

13. The subject information obtaining apparatus according to claim 1, wherein the first and second pressure distribution information is displayed in units of mmHg.

* * * * *